United States Patent [19]

Kimber

[11] Patent Number: 5,135,514
[45] Date of Patent: Aug. 4, 1992

[54] PLASTIC CARTRIDGE AND SYRINGE

[75] Inventor: Michael B. Kimber, Sidney, Australia

[73] Assignee: Astra Pharmaceuticals Pty Ltd, North Ryde, Australia

[21] Appl. No.: 307,632

[22] Filed: Feb. 7, 1989

[30] Foreign Application Priority Data

Feb. 10, 1988 [AU] Australia .............. 11603/88

[51] Int. Cl.$^5$ .............................. A61M 5/00
[52] U.S. Cl. ................... 604/240; 604/192; 604/263; 604/232
[58] Field of Search ............... 604/192, 200, 227, 236, 604/240, 244, 263, 232

[56] References Cited

U.S. PATENT DOCUMENTS

| 758,949 | 5/1904 | Apple et al. . | |
|---|---|---|---|
| 2,642,868 | 6/1953 | Pontius . | |
| 3,380,452 | 4/1968 | Elias | 604/240 |
| 3,390,678 | 7/1968 | Bradley et al. | 604/240 |
| 3,430,627 | 3/1969 | Kitaj | 604/240 |
| 3,945,383 | 3/1976 | Bennett et al. . | |
| 4,040,421 | 8/1977 | Young . | |
| 4,121,588 | 10/1978 | Geiger . | |
| 4,235,235 | 11/1980 | Bekkering . | |
| 4,281,653 | 8/1981 | Barta et al. | 604/240 |
| 4,747,839 | 5/1988 | Tarello et al. | 604/240 |

FOREIGN PATENT DOCUMENTS

| 233551 | 4/1960 | Australia . |
|---|---|---|
| 69468/74 | 12/1975 | Australia . |
| 22635/77 | 8/1978 | Australia . |
| 24642/77 | 11/1978 | Australia . |
| 27579/77 | 2/1979 | Australia . |
| 41625/78 | 5/1979 | Australia . |
| 86396/82 | 2/1983 | Australia . |
| 86779/82 | 2/1983 | Australia . |
| 86910/82 | 2/1983 | Australia . |
| 73632/81 | 10/1983 | Australia . |
| 0047398 | 3/1982 | European Pat. Off. . |
| 0047442 | 3/1982 | European Pat. Off. . |
| 538857 | 11/1931 | Fed. Rep. of Germany . |
| 809698 | 7/1949 | Fed. Rep. of Germany . |
| 1966623 | 8/1973 | Fed. Rep. of Germany . |
| 1040208 | 10/1953 | France . |
| 86/03126 | 6/1986 | PCT Int'l Appl. . |
| 1386030 | 3/1975 | United Kingdom . |

Primary Examiner—Stephen C. Pellegrino
Assistant Examiner—Michael Rafa
Attorney, Agent, or Firm—White & Case

[57] ABSTRACT

A plastic cartridge for use as a pre-filled cartridge comprising a hollow cylindrical barrel (1) having a top end and a bottom end (2) both of which are open. The bottom end is sealed by a stopper (3) and the top end (6) by a plastic cap (7). The cap comprises a hypodermic needle (27), or an integrally moulded fitting (12) adapted to receive a hypodermic needle, and a closure (9) which is frangibly connected and integral with the cap (7) so that upon application of a removal force on the closure the closure can be separated from the cap thus revealing the hypodermic needle or the hypodermic needle fitting and the contents of the cartridge. Also the prefilled syringe is described and a method for manufacturing the pre-filled cartridge.

15 Claims, 2 Drawing Sheets

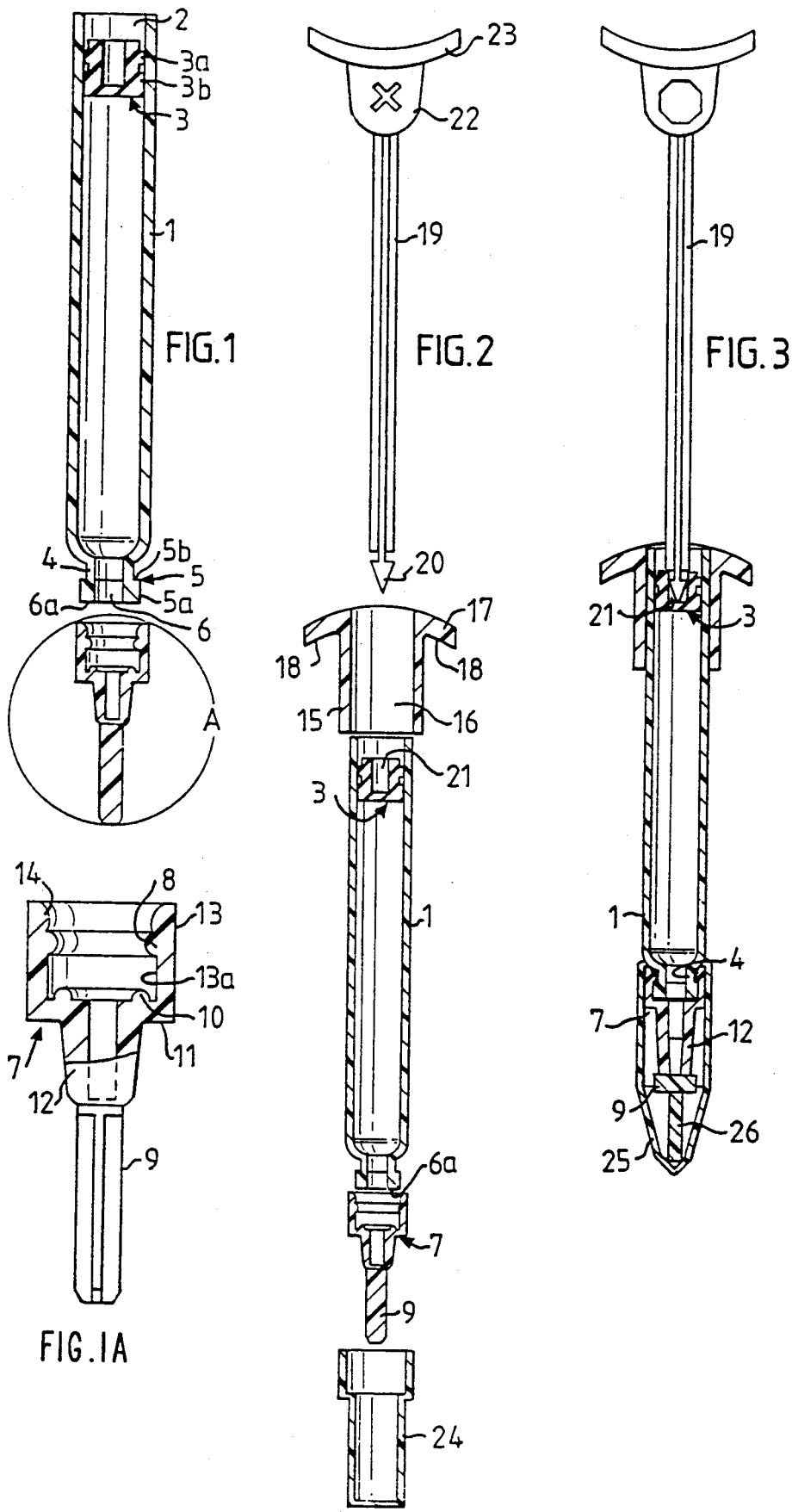

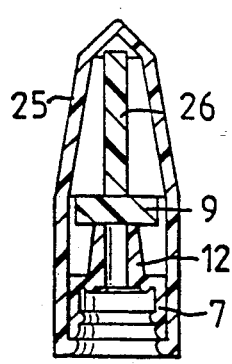
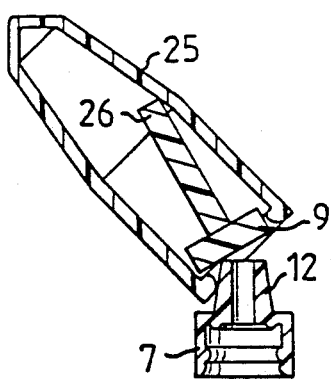
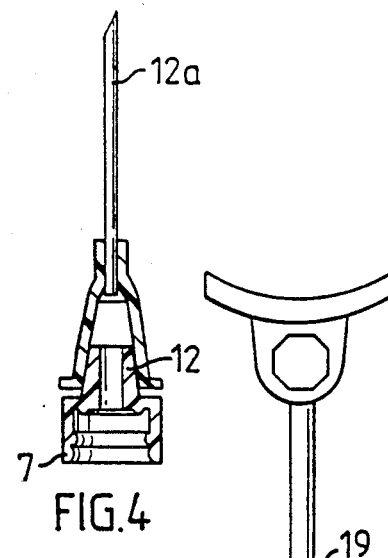
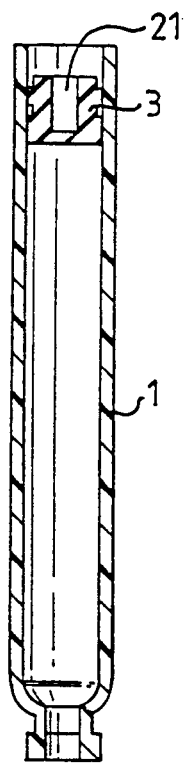
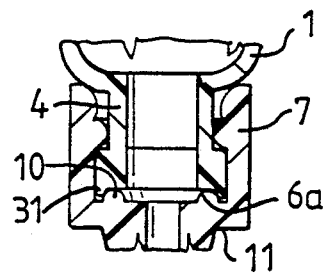
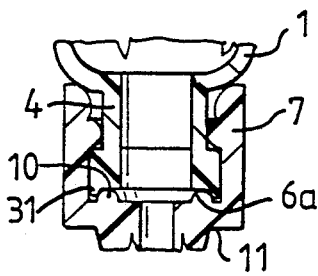
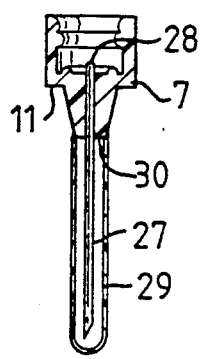

PLASTIC CARTRIDGE AND SYRINGE

FIELD OF THE INVENTION

This invention relates to a plastic cartridge construction for use as a prefilled plastic cartridge. The cartridge of the the invention can be used in conjunction with a finger grip, a plunger rod and a hypodermic needle as a syringe or can be used in place of a conventional cartridge in a syringe barrel. This invention also relates to a method of manufacturing such a cartridge.

BACKGROUND OF THE INVENTION

Many syringes in common use today utilize a glass or plastic pre-filled cartridge. Such cartridges are conventionally sealed at one end by a rubber stopper and at the other end by a rubber membrane which is sealed against the outside of the cartridge by a metal cap. The metal cap is crimped onto the end of the cartridge thus ensuring an effective seal at the end of the cartridge remote from the rubber stopper. One example of such a syringe is described in AU-A-73632/81.

Cartridges of the type described are conventionally filled with an injectable medium and may then be autoclaved to ensure the sterility of the contents. In use, these cartridges are inserted into a syringe holder designed to allow expression of the contents of the cartridge. For example, metal barrelled syringes having a fitting at one end to accept a double sided needle and a plunger at the other end have previously been in use. These syringes are intended for multiple use and must be stored in a sterilizing cabinet after each use. Furthermore, they suffer from the disadvantage that they are heavy and large. The size of the syringe is a particular disadvantage as these syringes are intimidating for patients. Also in use are disposable syringe bodies to which there is fixed a double sided needle. When these disposable syringe bodies are used a pre-sterilized cartridge is inserted into the syringe body. The double sided needle is adapted to puncture the rubber membrane at the end of the cartridge barrel and a plunger rod is used to expel the contents of the cartridge.

The cumbersome nature of prior syringe assemblies has lead to various alternative assemblies being investigated with a particular view to designing a simple disposable syringe and cartridge. For example, in Australian patent specification 468,624 there is described a disposable syringe assembly having a barrel molded from a plastics material. This syringe however continued the use of double ended needles and required the use of an external shell for the mounting of the cannula. An alternative arrangement also using a double ended needle is disclosed in AU-A41625/78. This syringe assembly utilized a double ended needle encased within a housing which was retained in a hub socket within which the needle housing was adapted to move. On the application of an inward force on the needle housing a diaphragm adjacent the hub was punctured by the rearward needle to reveal the contents of the cartridge for injection. This development also suffered from the disadvantage of having to provide an internal diaphragm within the cartridge and the use of a double ended needle. Similar use of a puncturable diaphragm in conjunction with a spike for revealing the contents of a pre-filled syringe can be seen by reference to AU-A27579/77. It has also been common practice to utilize a needle guard and these guards have usually conveniently slipped over the needle fitting (for example see FIG. 1 of AU-B86910/82). Such needle guards are usually frictionally fitted over the needle fitting. In WO86/03126 there is disclosed a syringe which incorporates a retaining clip to hold a separate needle fitting in position over the end of an injection body having a specially moulded needle fitting seat. The retaining clip incorporates a protective sheath which is frangibly connected to the body of the clip. However, the syringe assembly described in WO86/03126 suffers from the disadvantage of requiring a specially moulded seat for retaining the hypodermic needle fitting and a retaining clip to hold the needle in place. This limits use of the syringe to needles which can be fitted into the moulded seat and sealing requires the use of a separate sealing ring.

OUTLINE OF THE INVENTION

The object of the present invention is to provide a pre-filled plastic cartridge which can be used in existing syringe bodies or preferably be used as a component part of a disposable syringe unit.

In accordance with the present invention there is provided a plastic cartridge for use as a pre-filled cartridge comprising a hollow cylindrical barrel having a top end and a bottom end both ;of which are open wherein said bottom end is sealed by a stopper and said top end is sealed by a plastic cap, said cap comprising a hypodermic needle, or an integrally moulded fitting adapted to receive a hypodermic needle, and a closure which is frangibly connected and integral with said cap so that upon application of a removal force on the closure the closure can be separated from the cap thus, revealing the hypodermic needle or the hypodermic needle fitting and the contents of the cartridge.

The barrel may be made of any rigid plastics material. For example, a translucent or transparent plastics material such as polyethylene terephthalate, polyamide, polypropylene or TPX may be used. Other suitable materials are well known to those skilled in the art. Most preferably, polypropylene is used as this material is of relatively low cost, has a clear finish and is a well tested material for containing pharmaceutical substances.

At the top end of the barrel, there is preferably provided a neck portion having a diameter smaller than the diameter of the major portion of the cartridge barrel.

At the end of the neck portion there is preferably provided an upper annular face, an outer neck wall and an abutment shoulder. These surfaces may be constituted by a flange provided on the cartridge neck and may be in the form of a circumferential ring or rib. In one form of the invention, a cartridge end rib is also provided about the upper annular face (preferably about its perimeter). This rib of plastics material is adapted to melt on welding of the cartridge cap to the top end of the barrel to form a sealing ring. This rib may be shaped to co-operate with an annular rib on the underside of the cartridge cap (as hereinbefore described) to provide a broader sealing ring on welding or alternatively may be utilized with a cartridge cap without such an annular rib where it provides a narrow yet firm sealing ring.

The cartridge barrel is sealed at the bottom end by a stopper. The stopper may be of any known type and has an inner face facing internally into the cartridge body and an outer face facing out of the cartridge body. Preferably the stopper is a resilient stopper and may be made from a rubber compound. Preferably the stopper has at least two circumferential sealing rings to assist in maintaining a fluid tight seal at the bottom end of the cartridge barrel. The stopper preferably also has a plunger retaining recess centrally located in the end of the stopper.

The cartridge cap is also made of a plastics material and preferably comprises a top and a depending peripheral skirt.

The peripheral skirt is rigid and adapted to fit over the top end of the cartridge barrel. The cap is sealingly affixed to the cartridge barrel and this may be effected using an adhesive or most preferably by welding the cap to the top of the cartridge barrel.

Preferably the cartridge barrel has a neck portion and a flange on the neck portion. In such an embodiment the peripheral skirt is desirably adapted to clip over the top of the flange on the neck of the cartridge barrel so to retain the cap firmly in place over the top end of the barrel. Once in place, the depending peripheral skirt is preferably in contact with the outer neck wall on the neck of the cartridge and the bottom of the peripheral skirt is clipped over and is in contact with the abutment shoulder on the neck. The cap may also have an annular shoulder located on the inside of the peripheral skirt to clip over the flange on the neck of the cartridge barrel. The cap may be welded or otherwise adhered to the cartridge barrel neck.

In one embodiment of the invention the cartridge cap is also provided with an annular rib on the underside of the top portion of the cap. In this embodiment the cap is fitted onto the top of the cartridge barrel and is then ultrasonicly welded to the barrel. Preferably the annular rib is located to abut against the upper annular face on the end of the neck of the cartridge barrel. If the upper annular face also comprises an end rib as previously described, the annular rib is positioned on the underside of the cap to lap the end rib. In this way, when the ribs soften on welding they join not only the cap to the cartridge but also join together to form a broader sealing ring. By applying the horn and anvil of the ultrasonic welder on opposite sides of the annular and cartridge end ribs the ribs are caused to soften thus providing the material to form a sealing ring between the cartridge cap and barrel. Alternatively the cartridge cap may be contact or otherwise butt welded to the cartridge barrel.

The cap may be made of any suitable plastics material but is preferably made of an elastomer such as polypropylene or polyethylene The cap also comprises a hypodermic needle, or an integrally moulded fitting adapted to receive a hypodermic needle, and a top closure which is integral with the cartridge cap but which is frangibly connected thereto so that application of a removal force on the closure will cause the said closure to sever from the cartridge cap thus revealing the hypodermic needle or the hypodermic needle fitting and the contents of the cartridge for injection Where the cartridge cap has an integrally moulded needle fitting this fitting is preferably of standard configuration such as a screw thread fitting as often used by dentists or a luer slip or luer lock arrangement.

The closure is frangibly connected to the top of the needle fitting in this case so that upon removal the needle finish is exposed. Whilst the closure is frangibly connected it maintains a complete seal with the rest of the cartridge cap prior to removal so that the contents of the cartridge are maintained in a fluid tight and aseptic condition.

Where the cartridge cap includes a hypodermic needle the bottom end of the needle protrudes beneath the underside of the top of the cap so that it is in fluid communication with the cartridge barrel The hypodermic needle is preferably fixed within the cartridge cap and moulded therein. The closure fits over the top of the hypodermic needle and is frangibly connected to the rest of the cartridge cap so that the contents of the cartridge are manufactured in a fluid tight condition.

The closure may be moulded to a shape adapted to accommodate a similarly shaped spanner for ease of removal. Once the closure is removed the hypodermic needle or the needle fitting on the cartridge cap is exposed. Where a needle fitting is moulded into the cap removal of the closure exposes the needle fitting and an appropriate hypodermic needle having a corresponding fitting is easily attached to the exposed needle fitting. Removal of the closure also opens the cartridge enabling the injectable medium to be expressed through the hypodermic needle upon application of an adequate force on the stopper located in the bottom end of the cartridge barrel.

The cap closure may also be provided with an integral stem. Such a stem provides a user with the benefit of a lever action on the closure so providing easier removal of the closure. Further, an overcap may also be provided. An overcap is useful in keeping the cap protected from undue interference whilst the cartridge is not in use. Such an overcap is employed primarily however to protect the end of the cartridge from becoming contaminated by micro-organisms. It is also useful in the embodiment previously described wherein the cap is provided with a closure having an integrally attached stem portion.

In such an embodiment the overcap once fitted can be tilted to one side thus acting upon the stem portion of the cartridge cap. This enables one action removal of the overcap and cap closure by application of a lateral force against the side of the overcap. The overcap coacts against the stem thus facilitating a snap off removal of the cap closure.

The cartridge described above in any of its embodiments can be used in existing syringe barrels (with the necessary modifications) or can itself be used as a component part of a syringe unit.

Where used as a component part of a syringe unit it is necessary that the cartridge be fitted with a finger grip. Preferably the finger grip is a plastic sleeve shaped component having a flange sufficiently wide for accommodating a finger on either side of the cartridge barrel. Such a finger grip is also preferably made of an elastomer such as polypropylene, polyethylene of polyethylene terephthalate. The finger grip is adhered to the side of the cartridge, preferably by welding same to the plastic cartridge barrel.

In the total syringe unit it is also necessary to have a plunger rod. The plunger rod may have a variety of moulded ends, such as a screw thread to allow positive aspiration; or a blunt end to allow self aspiration during injection. The opposite end of the plunger rod may conveniently have a spanner fitting moulded into it for removing the cap closure. The spanner fitting at the end of the plunger rod is advantageous as it allows the user to employ the mechanical advantage provided by the length of the plunger rod.

In use the cartridge/syringe unit is assembled by inserting the plunger rod into the stopper sealing the bottom end of the cartridge. The closure forming part of the cartridge cap is then removed by applying an appropriate force thereto and a hypodermic needle is then applied to the needle fitting on the cartridge cap (where required). A single sided needle is adequate but the closure must be removed prior to application of the hypodermic needle. Removal of the closure reveals the contents of the cartridge. Application of a force against the plunger rod causes positive forward movement of the stopper in the cartridge barrel thus causing expression of the injectable through the hypodermic needle. In this form there is provided an all plastic (other than cannula) hypodermic syringe which is easy to use and which is disposable after a single use.

Method of Manufacture

The present invention also encompasses a method of manufacturing such a cartridge unit.

According to this aspect of the invention a cartridge barrel and cartridge cap as hereinbefore described are injection moulded in an aseptic environment, a pre-sterilized stopper is introduced into the aseptic environment and is fitted into the bottom end of the cartridge barrel to seal same. The cartridge barrel is then aseptically filled with the proposed injectable medium and then sealed by affixing the cartridge cap to the top end of the filled cartridge barrel.

The cartridge cap is preferably affixed to the cartridge barrel by welding it to the barrel. Butt welding or ultrasonic welding techniques can be usefully employed to effect this fixation. Preferably, an overcap is also injection moulded in the aseptic environment as well. Where an overcap is also moulded this component is fixed over the top of the cartridge cap after the cartridge cap has been affixed to the cartridge barrel The overcap can alternatively be supplied to the aseptic environment in a pre-sterilised form.

BRIEF DESCRIPTION OF THE DRAWINGS

A preferred embodiment of the invention is hereafter described with reference to the following drawings in which:

FIG. 1 is a cross-sectional exploded view of a cartridge made in accordance with the present invention having a luer slip needle fitting.

FIG. 1A is an enlarged detailed view of the area labelled "A" in FIG. 1.

FIG. 2 is a cross-sectional exploded view of a syringe unit utilizing the cartridge shown in FIG. 1.

FIG. 3 is a cross-sectional assembled view of a syringe unit utilizing the cartridge shown in FIG. 1.

FIG. 3a is a cross-sectional view of a cartridge cap and overcap as utilized in a particular embodiment of the invention.

FIG. 4 is a cross-section view of a cartridge cap with a luer slip finish having a hypodermic needle fitted thereto.

FIG. 5 is a cross-sectional assembled view of a cartridge made in accordance with the present invention having a screw threaded needle fitting.

FIG. 6 is a cross-sectional exploded view of a cartridge made in accordance with the present invention having a hypodermic needle fixed within the cartridge cap.

FIG. 7 is a cross-sectional view of the neck of the cartridge with the cap fitted thereto prior to affixation by ultrasonic welding in accordance with the invention.

DETAILED DESCRIPTION OF THE INVENTION

In FIG. 1 there is shown a cartridge barrel 1. Cartridge barrel 1 is made of a plastics material, most preferably polypropylene. At the bottom end of barrel 1 there is an open end 2 into which there is inserted a stopper 3. Stopper 3 is adapted to move within barrel 1 whilst retaining a fluid tight seal. To this end, stopper 3 is preferably made of rubber and has two sealing rings 3a and 3b. At its top end cartridge barrel 1 has a neck 4 of smaller diameter than the rest of the cartridge barrel body. At the end of neck 4 there is provided a flange 5. At the end of the neck portion there is provided an upper annular face 6a, an outer neck wall 5a and an abutment shoulder 5b. At the edge of upper annular face 6a, there is provided a cartridge end rib 31 (see FIG. 7). The cartridge barrel 1 is open at the top end at open end 6.

A cartridge cap 7 is provided, which is adapted to be sealingly attached to the neck 4 of cartridge barrel 1. Cartridge cap 7 is shown in greater detail in the enlargement "A" to FIG. 1. This cap has an annular shoulder 8 adapted to clip over flange 5 on neck 4. When the cap is clipped into place over neck 4 the inside face 13a of depending peripheral skirt 13 contacts outer neck wall 5a and annular shoulder 8 clips over and is in contact with abutment shoulder 5b on the neck (see FIG. 4). A X-formed closure fitting 9 is integrally attached to the cartridge cap 7 to ensure complete evacuation of the contents of cartridge barrel 1. An annular rib 10 is provided on the underside of the top 11 of cartridge cap 7. This annular rib 10 is provided on the underside of the top 11 of cartridge cap 7 and is located so that it abuts against the top of the neck 4 and laps the side of cartridge end rib 31 when the cartridge cap 7 is clipped onto the top of cartridge barrel 1. A standard luer slip finish 12 is provided as part of cartridge cap 7.

Assembly of the cartridge is preferably as follows. The cartridge cap and overcap are injection moulded from sterile plastic material, the injection moulding machine being situated in an aseptic area. Cartridge barrel 1 is stoppered with a pre-sterilized stopper at the open end 2 and is then aseptically filled. After the cartridge has been filled the cartridge cap 7 is clipped onto neck 4, annular shoulder 8 seating beneath flange 5 and in contact with abutment shoulder 5b. A fluid tight seal is ensured by welding cartridge cap 7 to cartridge barrel 1. In the embodiment shown this is effected by ultrasonic welding. A welding horn is placed on top 11 above annular rib 10 and cartridge end rib 31 and a welding anvil is placed under the bottom lip 14 of depending peripheral skirt 13. Ulstrasonic welding causes annular rib 10 and cartridge end rib 31 to melt and form a broad sealing ring between cartridge cap 7 and the top of neck 4.

In use, closure 9 is severed from the top of cartridge cap 7 revealing the contents of the cartridge and exposing the luer slip finish 12 for attachment of a standard needle fitting having a luer finish This cartridge may be used in syringe assemblies which are presently available (with minor adjustments to the top end of the assembly to accommodate the cartridge cap) or as a component in a disposable syringe unit.

A disposable syringe unit utilizing the cartridge illustrated in FIG. 1 is shown in an exploded view in FIG. 2.

Cartridge barrel 1 and cap 7 are illustrated in FIG. 2. A finger grip 15 is provided at the bottom end of the cartridge body 1. The finger grip 15 has a hollow sleeve 16 shaped to fit over the end of cartridge barrel 1. The finger grip may be adhered to the cartridge barrel 1 but is preferably welded thereto. Finger grip 15 is provided with an arm 17 which protrudes over opposite sides of sleeve 16 to provide a gripping area 18 on either side of cartridge barrel 1. A plunger rod 19 is also provided and has a moulded end 20 adapted to fit into a recess 21 provided in stopper 3. An alternative to the molded end 20 as shown in FIG. 2 is to provide a screw thread fitting at the end of plunger rod 19 adapted to screw into a corresponding screw thread in recess 21. At the opposite end of plunger rod 19 there is provided a spanner fitting 22 of X-formed shape adapted to co-operate with closure 9. A handle 23 is located at the end of plunger rod 19 so to enable pressure to be applied to plunger rod in the axial direction of the cartridge barrel 1. A protective cap 24 is provided at the top end to fit over and protect the cap 7.

FIG. 3 shows the above described syringe unit in an assembled condition utilizing a modified cap and overcap 25 As illustrated cap 7 is clipped onto the neck 4 of cartridge barrel 1. The closure 9 on cap 7 comprises an integral stem 26. Overcap 25 is clipped over the top of cap 7, stem 26 and neck 4.

In use the plunger rod 19 is inserted into recess 21 in stopper 3. In the embodiment shown in FIG. 3, a lateral force is applied to overcap 25. This force acts upon stem 26 thus causing closure 9 to snap off the top of needle fitting 12. This is more conveniently seen in FIG. 3(a). Once closure 9 has been broken off cap 7, needle fitting 12 is exposed for receiving a needle having a luer slip configuration. FIG. 4 shows a hypodermic needle 12a once fitted over needle fitting 12. The removal of closure 9 also exposes the contents of cartridge barrel 1 for injection The hypodermic needle 12a once fitted, sealingly fits over the luer slip finish on cap 7 and positive pressure on plunger rod 19 causes stopper 3 to advance in cartridge barrel 1 causing the injectable medium to be expressed through hypodermic needle 12a.

In use the embodiment shown in FIG. 2 operates in the same way as that shown in FIG. 3 except that the closure is removed by snap action preferably with the aid of spanner fitting 22 located at the end of plunger rod 19.

In FIG. 5 there is illustrated a syringe unit which is the same in all respects as that illustrated in FIG. 3 except that a different needle fitting 12 is moulded into cap 7. In this embodiment a screw thread needle fitting 12 is moulded into cap 7. In the same way as described above closure 9 is removed from the needle fitting and cap 7 by application of a force on the closure, either by hand, by use of a spanner or by use of an overcap co-operatively arranged to coact against a stem 26 integrally attached to the said closure 9.

FIG. 6 illustrates a cartridge barrel 1 capped by a cap 7 having a hypodermic needle 27 fixedly held therein. The hypodermic needle 27 has a first end 28 proximate the top end of the cartridge barrel 1. This end 28 protrudes through the underside of top 11 so to be in fluid communication with the contents of cartridge barrel 1. Closure 29 is a solid stem of plastics material which encapsulates hypodermic needle 27 above weakened section 30. In use, plunger rod 19 is inserted into recess 21 in stopper 3 as in earlier embodiments. Closure 29 is then separated from the rest of cap 7 by application of an upward or rotating force. Closure 29 snaps off from the rest of cartridge cap 7 at weakened section 30 to expose the top end of the hypodermic needle 27 and to also reveal the contents of the cartridge barrel 1 so that it is available for injection.

FIG. 7 illustrates the cartridge cap 7 in position over neck 4. Annular rib 10 and cartridge end rib 31 can be seen lapping each other providing the material for a broad sealing ring after the two Components are welded together.

In each of the embodiments described herein it is possible using the cartridge of the present invention to provide a disposable syringe which is easy to use and simple in application. There is no need to use a separate syringe holder and the cartridge can be provided to practitioners in a partially assembled condition with the finger grip already attached to the cartridge barrel. The only separate components being a plunger rod in the embodiment disclosed in FIG. 6 and described above and additionally a standard hypodermic needle in the case of those embodiments illustrated in FIGS. 2, 3 and 5.

Each of the above mentioned embodiments are either partially or completely manufactured in an aseptic environment to ensure the sterility of the injectable medium. For example in the embodiment illustrated in FIG. 3, cartridge barrel 1 is preferably injection moulded in an aseptic environment. Stopper 3 is then delivered to the aseptic environment in a pre-sterilized condition and inserted into the bottom end 2 of cartridge barrel 1. The cap 7 is also injection moulded in an aseptic environment. The cartridge barrel is stoppered then filled with the pre-sterilized injectable medium and is then capped by the injection moulded cap 7. The cap 7 is then welded or otherwise adhered to cartridge barrel 1. Overcap 25 is also injection moulded in the aseptic environment and is fitted over the closure 7 and neck 4 prior to removal of the cartridge from the aseptic conditions. When manufactured as described above it is important that the polymer beads used for the injection moulding process be pre-sterilized prior to injection moulding of the component part of the cartridge. Finger grip 15 and plunger rod 19 can be injection moulded outside of the aseptic environment as they are not placed in direct contact with the injectable medium.

The cartridge described above represents a unique product for use in delivering injectable substances. It provides many improvements over the cartridges in present use. In particular, the cartridge described does not suffer through use of multiple components such as metal caps and rubber membranes. As there is no rubber membrane the practitioner does not have to use a double sided needle. This overcomes two problems associated with the standard cartridges, namely blocked needles due to a core of rubber becoming lodged in the needle and leaking at the point of needle entry through the rubber membrane due to a bent needle.

Further, the cartridge can be used in a simple large or intimidating as existing syringes.

Finally, it is to be understood that various alterations, modifications and/or additions may be introduced into constructions and parts previously described without departing from the spirit or ambit of the invention.

I claim:

1. A cartridge for use a prefilled cartridge comprising:
   a hollow cylindrical plastic barrel (1) having a top end and a bottom end (2) both of which are open;
   a stopper (3) disposed in and sealing said bottom end; and
   a plastic cap (7) sealingly engaging said top end (6); wherein said plastic cap includes a passage communicating with the interior of the barrel, and comprises means for holding a hypodermic needle for discharging fluid from said barrel through said passage;
   a closure means for sealing said passage from outside air, wherein said closure means is frangibly connected and integral with said cap (7) so that upon application of a removal force on the closure means the closure means can be separated from the cap thus revealing the passage for discharging fluid in said barrel; wherein said closure means includes an integral stem (26) adapted to act as a lever for removal of the closure mans from the cap; and
   an overcap covering the cap and closure means and having an interior adapted to act against the stem such that, upon the application of a sufficient tilting force against the overcap and thereby the stem, the closure means becomes separated from the cap.

2. A plastic cartridge as claimed in claim 1 wherein said cap (7) comprises a top (11) and a depending peripheral skirt (13}, said depending peripheral skirt being adapted to fit over the top end (6) of the cartridge barrel (1).

3. A plastic cartridge as claimed in claim 2 wherein said top end (6) of the cartridge barrel (1) has a neck portion (4) having a diameter smaller than the diameter of the major portion of the cartridge barrel.

4. A plastic cartridge as claimed in claim 3 wherein said neck portion comprises a flange (5) and said cap (7) is adapted to clip over the flange so to retain the cap firmly in place over the top end (6) of the barrel (1).

5. A plastic cartridge as claimed in claim 4 wherein said cap (7) has an annular shoulder (8) located on the inside of the peripheral skirt (13) adapted to clip over the flange (5) on the said neck portion (4) of the cartridge barrel (1).

6. A plastic cartridge as claimed in claim 5 wherein said neck portion (4) comprises an upper annular face (6a), an outer neck wall (5a) and an abutment shoulder (5b) such that upon placement of the cap onto the top end of the cartridge barrel the annular shoulder (8) located on the inside of the peripheral skirt (13) of the cap is clipped over and abuts against the abutment shoulder (5b) on the neck portion (4).

7. A plastic cartridge as claimed in claim 6 wherein the underside of said top of the cap (11 abuts against the upper annular face (6a) of the neck portion.

8. A plastic cartridge as claimed in claim 21 comprising a weld formed between the top end of the cartridge barrel and the cap for sealing the cap tot he cartridge barrel.

9. A plastic cartridge as claimed in claim 8 wherein the cap (7) also comprises an annular rib (10) on the underside of the top portion (11) of the cap located so to abut against the upper annular face (6a) of the neck portion after application of the cap onto the end of the cartridge barrel and adapted to form a sealing ring between the underside of the top portion of the cap (11) and the upper annular face of the neck portion.

10. A plastic cartridge as claimed in claim 9 wherein the upper face (6a) comprises a cartridge end rib (31) located so to abut against the underside of the top portion (11) of cap (7) after application of the cap onto the end of the cartridge barrel and adapted to form a sealing ring between the underside of the top portion of the cap (11) and the upper annular face of the neck portion.

11. A plastic cartridge as claimed in claim 8 wherein the weld is an ultrasonically formed weld.

12. A prefilled syringe comprising a plastic cartridge as claimed in claim 1 fitted with an injectable medium, a finger grip (15) attached to the cartridge barrel (1), a plunger rod (19) adapted to cooperate with said stopper (3) located in the bottom end of the cartridge barrel and where said cartridge does not comprise a hypodermic needle, a hypodermic needle (12a) adapted to be attached to the cap after removal of the closure means (9) whereby after removal of the cartridge closure means, and the attachment of a hypodermic needle where necessary, application of a force against the plunger rod causes positive forward movement of the stopper in the cartridge barrel thus facilitating expression of the injectable medium through the hypodermic needle.

13. A prefilled syringe as claimed in claim 12 wherein said syringe is constructed of a plastics material.

14. A plastic cartridge according to claim 1, wherein the hypodermic needle holding means comprises an integrally molded fitting (12) adapted to receive a hypodermic needle.

15. A plastic cartridge according to claim 1, further comprising a hypodermic needle provided in the hypodermic needle holding means and sealed by the closure.

* * * * *

UNITED STATES PATENT AND TRADEMARK OFFICE
CERTIFICATE OF CORRECTION

PATENT NO. : 5,135,514
DATED : August 4, 1992
INVENTOR(S) : Michael B. Kimber

It is certified that error appears in the above-indentified patent and that said Letters Patent is hereby corrected as shown below:

Col. 2, line 25, delete ";";

Col. 4, line 6, after "barrel," insert --.--;

Col. 5, line 56, delete "FIG."3a is" and insert -- FIGs. 3a and 3b are--, and change "view" to --views--;

Col. 7, line 27, after "25" insert --.--;

Col. 8, line 62, after "simple," insert --disposable pre-filled syringe unit which is not as heavy,--;

Col. 9, line 13, after "means," insert --(9)--;

Col. 9, line 29, change "}" to --)--;

Col. 10, line 6, change "21" to --1--; and

Col. 10, line 8, change "tot he" to --to the--.

Signed and Sealed this

Twentieth Day of January, 1998

Attest:

BRUCE LEHMAN

*Attesting Officer*           *Commissioner of Patents and Trademarks*